United States Patent
Van Dooren et al.

(10) Patent No.: US 11,402,048 B2
(45) Date of Patent: Aug. 2, 2022

(54) EXPANSION JOINT

(71) Applicant: Borealis AG, Vienna (AT)

(72) Inventors: Piet Van Dooren, Kemzeke (BE); Peter Clymans, Meerle (BE); Nikolaos Vavizos, Linz (AT); Marc Jordens, Nijlen (BE); Matthias Weber, Bretten (DE); Marc Seckner, Karlsruhe (DE); Harald Betke, Pforzheim (DE); Peter Rittershofer, Pforzheim (DE); Bert Balmer, Pforzheim (DE); Jochen Senger, Ubstadt-Weiher (DE); Abdelkarim Oulad Abdellah, Borgerhout (BE)

(73) Assignee: BOREALIS AG, Vienna (AT)

( * ) Notice: Subject to any disclaimer, the term of this patent is extended or adjusted under 35 U.S.C. 154(b) by 297 days.

(21) Appl. No.: 16/619,276

(22) PCT Filed: Jun. 11, 2018

(86) PCT No.: PCT/EP2018/065254
§ 371 (c)(1),
(2) Date: Dec. 4, 2019

(87) PCT Pub. No.: WO2018/228957
PCT Pub. Date: Dec. 20, 2018

(65) Prior Publication Data
US 2020/0096147 A1 Mar. 26, 2020

(30) Foreign Application Priority Data
Jun. 14, 2017 (EP) .................................... 17175959

(51) Int. Cl.
*F16L 51/02* (2006.01)
*C07C 5/327* (2006.01)
*F16L 59/147* (2006.01)

(52) U.S. Cl.
CPC ............ *F16L 51/025* (2013.01); *C07C 5/327* (2013.01); *F16L 51/026* (2013.01); *F16L 51/027* (2013.01); *F16L 59/147* (2013.01)

(58) Field of Classification Search
CPC ..... F16L 51/025; F16L 51/026; F16L 59/147; F16L 51/027; C07C 5/327
See application file for complete search history.

(56) References Cited

U.S. PATENT DOCUMENTS 2,406,234 A * 8/1946 Marancik et al. .... F16L 51/026
285/96
2,506,293 A * 5/1950 Copeland .............. F22B 37/105
285/96

(Continued)

FOREIGN PATENT DOCUMENTS

CN 201129590 Y 10/2008
CN 101517304 A 8/2009

(Continued)

OTHER PUBLICATIONS

Extended European Search Report for Application No. 17175959.0-1754, dated Dec. 7, 2017.

(Continued)

*Primary Examiner* — Zachary T Dragicevich
*Assistant Examiner* — James A Linford
(74) *Attorney, Agent, or Firm* — Tarolli, Sundheim, Covell & Tummino LLP

(57) ABSTRACT

The invention relates to an expansion joint (1) for joining two adjacent parts of a pipe. The expansion joint (1) comprises an expansion bellows (5), an expanded wall (2) and an inner sleeve assembly (8). The expanded wall (2) comprises a first wall part (3) and a second wall part (4), wherein the first wall part (3) and the second wall part (4) are spaced apart from each other axially by an axial gap. The expansion bellows (5) is connected to the first wall part (3)

(Continued)

and to the second wall part (4) such that the axial gap between the first wall part (3) and the second wall part (4) is closed and such that the first wall part (3) and the second wall part (4) are connected flexibly. The expanded wall (2) and the inner sleeve assembly (8) limit at least one sealed chamber (9, 10) between each other, and the at least one sealed chamber (9, 10) is filled by a first gas.

13 Claims, 7 Drawing Sheets

(56) References Cited

U.S. PATENT DOCUMENTS

| | | | | |
|---|---|---|---|---|
| 2,666,657 | A | * | 1/1954 | Howard .................. F16L 11/14 285/49 |
| 4,045,056 | A | | 8/1977 | Kandakov et al. |
| 5,303,960 | A | | 4/1994 | Gaughan |
| 6,910,506 | B2 | | 6/2005 | Gabriel et al. |
| 7,284,771 | B2 | * | 10/2007 | Baumann ................ F01N 13/14 285/226 |
| 2015/0084328 | A1 | | 3/2015 | Kampfe et al. |

FOREIGN PATENT DOCUMENTS

| | | |
|---|---|---|
| CN | 106090514 A | 11/2016 |
| EP | 0028742 A1 | 5/1981 |
| EP | 0376839 A1 | 7/1990 |
| EP | 2203437 B1 | 11/2012 |
| FR | 2124846 A5 | 9/1972 |

OTHER PUBLICATIONS

Applicant: Borealis AG; Chinese Application No. 201880037884.4; Entitled: "Expansion Joint"; Chinese Office Action; dated Nov. 3, 2020; 24 pgs.

* cited by examiner

EXPANSION JOINT

FIELD OF THE INVENTION

The invention relates to an expansion joint for joining two adjacent parts of a pipe. In particular, said pipe can be part of a plant for producing propylene from propane gas, a process which is especially known under the Trademark CATOFIN®.

BACKGROUND OF THE INVENTION

An expansion joint for two adjacent parts of a pipe is an element which joins or connects the parts of the pipe in a flexible manner. In particular, an expansion joint can safely absorb heat-induced expansion and contraction of the adjacent parts of the pipe, e.g. to absorb vibration, to hold the parts together, or to allow a movement of the parts of the pipe due to thermal or mechanical stresses which can be compensated for by means of the expansion joint. Expansion joints are used e.g. in plants in which propylene can be produced from propane gas in a catalyst process by means of a dehydrogenation, wherein an amount of hydrogen is reduced in the propane. This process is an advantageous alternative to known production methods, which usually involve a cracking of crude oil in refineries. Typically, there can be more than 20 expansion joints in such a plant for producing propylene from propane gas, in particular about 10 expansion joints in an inlet region and about 10 expansion joints in an outlet region. The expansion joints are critical elements of the plant and must fulfil their functions at very high temperatures, extreme flow velocities, and large cyclic movements. The two most common types of expansion joints in the plant are arranged in areas of an inlet header and an outlet header of the plant.

Expansion joints are known, which comprise an expansion bellows and an expanded wall designed to protect the expansion bellows from corrosion and damage due to overheating. The expansion bellows is welded onto the expanded wall, e.g. of an inlet pipe. An inner sleeve creates a chamber that separates the process fluid from the expanded wall and the bellows. Typically, this chamber is separated into two smaller chambers on either side of the expanded wall, wherein the two smaller chambers are filled with an insulation material. Due to differing thermal expansion coefficients of the materials involved, the two ends of the inner sleeve cannot be sealed. As a result, an opening is created, which allows process fluid to escape into the chamber. This can lead to an increase of temperature and creates a risk of coking. To solve this problem, solutions are known, according to which a channel that is created in a middle area between the insulation material chambers is constantly flushed with fresh propane gas.

The fresh propane gas can enter a main flow channel for the process gas via the opening between the two ends of the inner sleeve. This can have a potential detrimental effect on the temperature of the process fluid and on the yield of producing propylene from the propane gas, due to the fact that the flushing fluid has to be at a lower temperature than the process fluid to provide cooling at the bellows. Furthermore, in the area of the expanded wall and the inner sleeve coking can occur due to hydrocarbon material stagnating in high-temperature dead zones that are created within the inner sleeve and the expanded wall. In particular, at temperatures above 480° C. some olefins and di-olefins can be produced. At these temperatures and with sufficient residence time the olefins and di-olefins can convert to coke.

SUMMARY OF THE INVENTION

It is an object of the present invention to provide an expansion joint for joining two adjacent parts of a pipe, wherein a bellows of the expansion joint is better protected from higher temperatures of a fluid flowing across the expansion joint and wherein coking is avoided.

The problem is solved by the subject matter according to the independent claims. The dependent claims, the following description and the drawings show preferred embodiments of the invention.

According to a first aspect of the invention, an expansion joint for joining two adjacent parts of a pipe. e.g. made of stainless steel, is provided. In particular, the two adjacent parts of the pipe can be part of a plant for producing propylene from propane gas, a process which is especially known under the Trademark CATOFIN®.

The expansion joint comprises an expansion bellows, e.g. made of stainless steel, an expanded wall and an inner sleeve assembly.

The expanded wall comprises a first wall part, e.g. made of stainless steel, and a second wall part, e.g. made of stainless steel. The first wall part and the second wall part are spaced apart from each other axially by an axial gap. In particular, a first end face of the first wall part can face a second end face of the second wall part, wherein said first end face and said second end face are spaced apart from each other by the axial gap. In this context, the feature "expanded wall" particularly can mean that the wall is expanded in a radial direction compared to the two parts of the pipe, respectively, which can be joined by the expansion joint. In other words, the diameter of the expanded wall can be larger than the diameters of the two parts of the pipe of the pipe system which can be joined by the expansion joint.

The first wall part of the expanded wall can be mechanically connected to one of the two adjacent parts of the pipe, and the second wall part of the expanded wall can be mechanically connected to the other one of the two adjacent parts of the pipe. Alternatively, the first wall part of the expanded wall can be a part of one of the two adjacent parts of the pipe, meaning that the first wall part and one of the two adjacent parts of the pipe are connected to each other in a one-piece manner. Similarly, the second wall part of the expanded wall can be a part of the other one of the two adjacent parts of the pipe, meaning that the second wall part and the other one of the two adjacent parts of the pipe are connected to each other in a one-piece manner.

The expansion bellows is connected to the first wall part, in particular welded onto the first wall part, and connected to the second wall part, in particular welded onto the second wall part, such that the axial gap between the first wall part and the second wall part is closed and such that the first wall part and the second wall part are connected flexibly. in this context, the feature "connected flexibly" can especially mean that the first wall part and the second wall part are connected such that stresses caused by axial, angular and lateral movements between the first wall part and the second wall part can be compensated for, wherein said stresses can occur due to high temperatures (e.g. 650° C.) and high pressures (e.g. 2.9 bar) of propane gas flowing across the expansion joint during producing propylene from propane gas. Similar to the first wall part and the second wall part, the expansion bellows can be designed in an expanded manner with regards to a radial direction compared to the two parts of the pipe, which can be joined by the expansion joint. In other words, the diameter of the expansion bellows can be larger than the diameters of the two parts of the pipe which can be joined by the expansion joint.

The expanded wall and the inner sleeve assembly limit at least one sealed chamber between each other, and the at least one sealed chamber is filled by a first gas. In particular, the sealed chamber can be adapted to be filled and to be pressurized by the first gas. In other words, the expansion joint according to the first aspect of the invention, comprises a sealed chamber arrangement, in particular a pressurized sealed chamber arrangement, which enables that the expansion bellows is protected from a high temperature of a process fluid flowing across a flow channel within the expansion joint.

The at least one sealed chamber helps to eliminate the presence of hydrocarbon in an area of the expansion bellows, thus helping to eliminate the potential for damage due to coke formation. The at least one sealed chamber can extend across the whole circumference of the expansion joint, meaning that the at least one sealed chamber extends 360° in a circumferential direction. The expansion joint according to the first aspect of the invention can particularly be used both in an inlet section as well as in an outlet section of a plant for producing propylene from propane gas, wherein a same expansion joint can be employed albeit at different sizes.

According to an embodiment, the inner sleeve assembly comprises a first metal part, e.g. made of stainless steel, and a second metal part, e.g. made of stainless steel. The first metal part is connected to the first wall part, in particular welded onto the first wall part, such that the first metal part and the first wall part limit a first sealed chamber between each other. Similarly, the second metal part can be connected to the second wall part, in particular can be welded onto the second wall part, such that the second metal part and the second wall part limit a second sealed chamber between each other. The first sealed chamber and the second sealed chamber are filled by the first gas. In particular, the first sealed chamber and the second sealed chamber are adapted to be filled and to be pressurized by the first gas. If the first sealed chamber and the second sealed chamber are filled, and preferably also pressurised by the first gas, they are able to balance stresses during temperature cycles of a process gas flowing across the pipes and the expansion joint.

The at least one sealed chamber, in particular the first sealed chamber and the second sealed chamber, can be filled with insulating material. This helps to further protect the expansion bellows from high temperatures within the flow channel.

According to another embodiment, the inner sleeve assembly, in particular its first metal part and its second metal part, the expanded wall, in particular its first wall part and its second wall part, and the expansion bellows limit a third chamber between each other. The third chamber is adapted to be filled and pressurized with a second gas, such that an over pressure within the third chamber is higher than a process pressure of the second gas within a flow channel within the expansion joint. The flow channel is limited by the inner sleeve assembly, in particular a first interior wall surface provided by the first metal part and a second interior wall surface provided by the second metal part.

In particular, the third chamber can be located between the first sealed chamber and the second sealed chamber in an axial direction of the expansion joint. The third chamber is in fluid connection with the flow channel which enables second gas from within the third chamber to leave the third chamber and to enter the flow channel. Due to the higher pressure within the third chamber compared to the flow channel, second gas from within the flow channel is hindered to enter the third chamber.

In other words, the third chamber can be filled with and pressurized by the second gas, such that the second gas builds a barrier flow for the gas within the flow channel and that the third chamber acts as an hyperbaric pressure chamber compared to the flow channel. This helps to keep the hot gas within the flow channel away from the expansion bellows. Also, this helps to prevent the occurring of carbonization within the third chamber, which could lead to an undesired clogging within the third chamber. According to a preferred embodiment, the second gas is the same sort of gas that flows through the flow channel, i.e. the process gas, in particular propane gas.

According to another embodiment, the first metal part comprises a first additional bellows and the second metal part comprises a second additional bellows. The first additional bellows and the second additional bellows help to compensate for stresses that the pipes, the first metal part and the second metal part (which can be relatively thin compared to the pipes) are subjected to, in particular in areas of the first interior wall surface and the second interior wall surface.

According to another embodiment, the first wall part comprises a first retaining ring assembly and the second wall part comprises a second retaining ring assembly. The first retaining ring assembly separates the first sealed chamber from the third chamber and the second retaining ring assembly separates the second sealed chamber from the third chamber. Furthermore, the first retaining ring assembly and the second retaining ring assembly can comprise monolithic parts. The inventors found out and verified by simulation that these monolithic parts enable that the first metal part and the second metal part withstand high temperature stresses which occur during process cycles within a plant for producing propylene from propane gas. At the same time, simulations showed that temperatures reaching the expansion bellows do not exceed a design temperature of the material of the expansion bellows.

Furthermore, the first metal part can be bent 180° in a first bending area and the second metal part can be bent 180° in a second bending area, wherein the first bending area of the first metal part overlaps the second bending area of the second metal part such that pressurised second gas from within the third chamber can flow out of the third chamber into the flow channel. In particular, there can be a radial gap between the first bending area of the first metal part and the second bending area of the second metal part such that a connection channel for the second gas is built that allows second gas from within the third chamber to exit the third chamber and enter the flow channel via said connection channel. Due to the 180° bending, the first and second bending area are designed in a particular strength manner and can resist high stresses.

According to another embodiment, a first end of the first metal part is connected to, in particular welded onto the first wall part at a first connection position, a second end of the first metal part is connected to, in particular welded onto the first wall part at a second connection position, and a first portion of the first metal part between the first connection position and the first bending area provides a first interior wall surface of the flow channel. Similarly, according to this embodiment, a first end of the second metal part is connected to, in particular welded onto the second wall part at a third connection position, a second end of the second metal part is connected to, in particular welded onto the second wall part at a fourth connection position, and a first portion of the second metal part between the third connection position and the second bending area provides a second interior wall surface of the flow channel.

According to this embodiment, the inner sleeve of the expansion joint is formed by the first metal part, in particular by its first portion between the first connection position and the first bending area, and the second metal part, in particular by its first portion between the third connection position and the second bending area. Therefore, the first metal part serves to build the first sealed chamber as well as a part of the inner sleeve assembly, and the second metal part serves to build the second sealed chamber as well as another part of the inner sleeve assembly. Due to their aforesaid double functions, there is no need for an additional element which forms the inner sleeve assembly. Thus this embodiment helps to save parts, weight, manufacturing affords and costs.

The expansion joint can further comprise first means for sensing pressure and second means for sensing pressure, wherein the first means for sensing pressure are adapted for measuring a first pressure, in particular a first pressure value, within the first sealed chamber, and wherein the second means for sensing pressure are adapted for measuring a second pressure, in particular a second pressure value, within the second sealed chamber. In case a potential leak occurs in the first sealed chamber or the second sealed chamber, such a leak can be monitored by means of the first or the second means for sensing pressure, respectively, wherein a loss of pressure within the respective sealed chamber can indicate the leak. Said loss of pressure can be determined e.g. by comparing a pressure value sensed at a first moment of time with a second pressure value sensed at a second moment of time, wherein the second moment of time lies before the first moment of time. Furthermore the first means for sensing pressure and the second means for sensing pressure can be adapted for generating data representing the measured pressure values, wherein the generated data can be transmitted e.g. to an electronic control unit for controlling a filling and pressurizing of the first sealed chamber and/or the second sealed chamber with the first gas.

Furthermore, the expansion joint can comprise first gas supply means and second gas supply means, wherein the first gas supply means are adapted for filling and preferably also for pressurising the first sealed chamber with the first gas, and wherein the second gas supply means are adapted for filling and preferably also for pressurising the second sealed chamber with the first gas.

In particular, if the first means for sensing pressure have measured a loss of pressure within the first sealed chamber, the first gas supply means can be adapted for refilling and re-pressuring the first sealed chamber with a sufficient amount of the first gas, such that the loss of pressure is compensated for. During such a refilling and a re-pressuring, the first means for sensing pressure can be adapted for sensing, preferably in a continuous manner, the pressure within the first sealed chamber. Preferably, an electrical control unit can be adapted for automatically controlling said refilling and re-pressuring. During such a controlling, especially the pressure value within the first sealed chamber measured by the first means for sensing pressure can be used as an input for the controlling. Furthermore, after said refilling and re-pressuring has been conducted, the first means for sensing pressure can sense the pressure within the first chamber again, such that a potential leak in the first chamber is searched for again.

Similarly, if the second means for sensing pressure have measured a loss of pressure within the second sealed chamber, the second gas supply means can be adapted for refilling and re-pressuring the second sealed chamber with a sufficient amount of the first gas, such that the loss of pressure is compensated for. During such a refilling and a re-pressuring, the second means for sensing pressure can be adapted for sensing, preferably in a continuous manner, the pressure within the second sealed chamber. Preferably, an electrical control unit can be adapted for automatically controlling said refilling and re-pressuring. During such a controlling, especially the pressure value within the second sealed chamber measured by the second means for sensing pressure can be used as an input for the controlling. Furthermore, after said refilling and re-pressuring has been conducted, the second means for sensing pressure can sense the pressure within the second chamber again, such that a potential leak in the second chamber is searched for again.

According to another embodiment, the expansion joint further comprises third gas supply means, wherein the third gas supply means are adapted for filling and pressurising the third chamber up to the over pressure with the second gas. In particular, the third gas supply means can comprise at least one purge channel in fluid connection with the third chamber and a reservoir for storing the second gas in a pressurized manner, wherein second gas stored within the reservoir can enter the third chamber via the at least one purge channel for filling and pressurising the third chamber up to the over pressure with the second gas.

Preferably, the first gas is nitrogen. Also preferably, the second gas is propane gas.

According to still another embodiment, the inner sleeve assembly, and the expanded wall can at least partly be formed integrally as a one piece element. This helps to increase the stability of the expanded wall and the inner sleeve assembly and particularly increases the tightness of the at least one sealed chamber due to the advantage that especially less weld seams unnecessary to connect the inner sleeve assembly to the expanded wall.

According to a second aspect of the invention, a plant for producing propylene from propane gas is provided. The plant comprises a first part of a pipe, a second part of the pipe and an expansion joint according to the first aspect of the invention, wherein the first part of the pipe is joined to the second part of the pipe by means of the expansion joint.

These and other aspects of the invention will be apparent from and elucidated with reference to the embodiments described hereinafter.

BRIEF DESCRIPTION OF THE DRAWINGS

In the following description exemplary embodiments of the invention are explained with reference to the accompanying drawing in which.

DETAILED DESCRIPTION OF EXEMPLARY EMBODIMENTS

Figure 1:
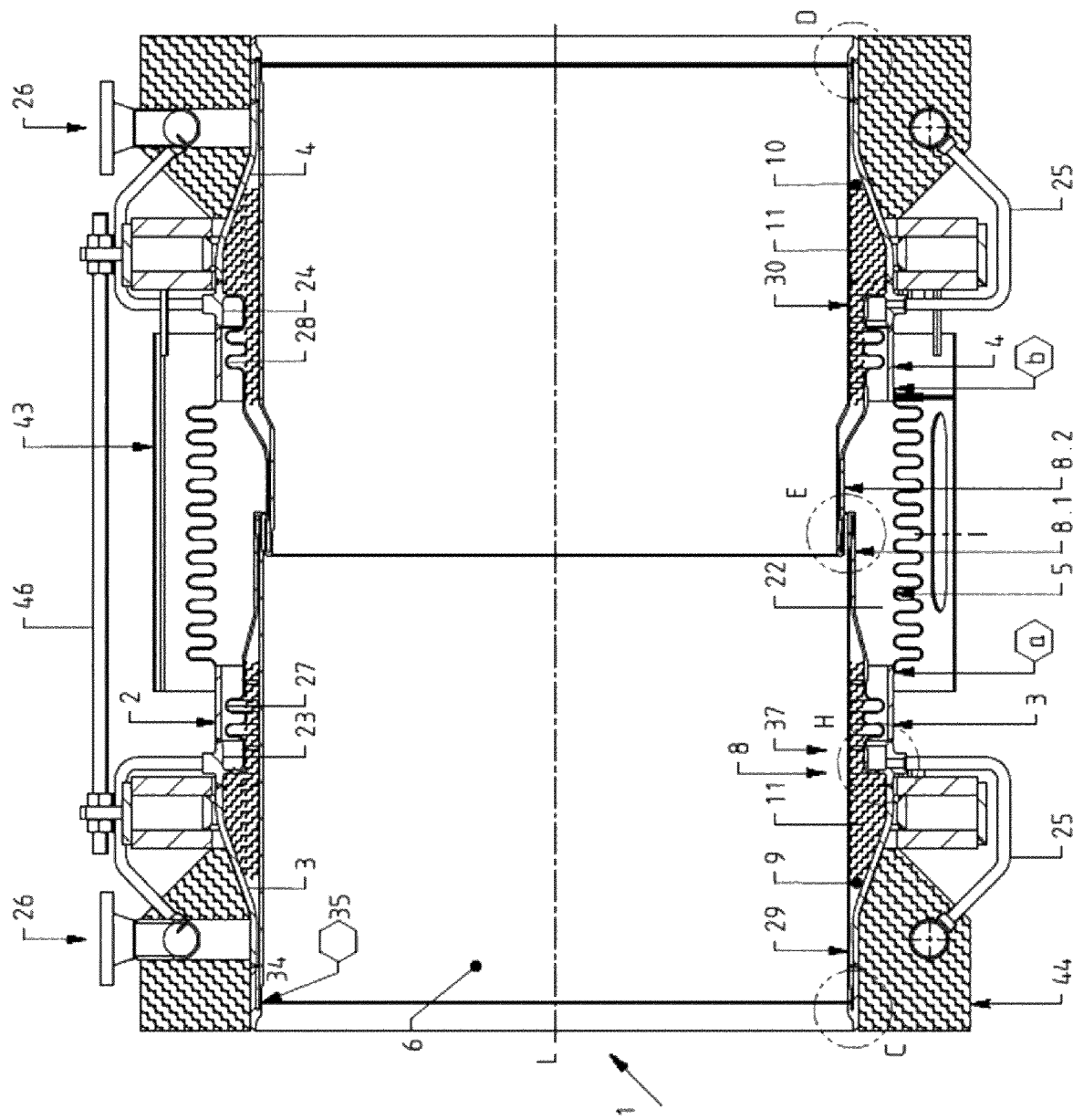
FIG. 1 shows a cross-sectional view of an expansion joint in accordance with an embodiment of the invention.
Figure 2:
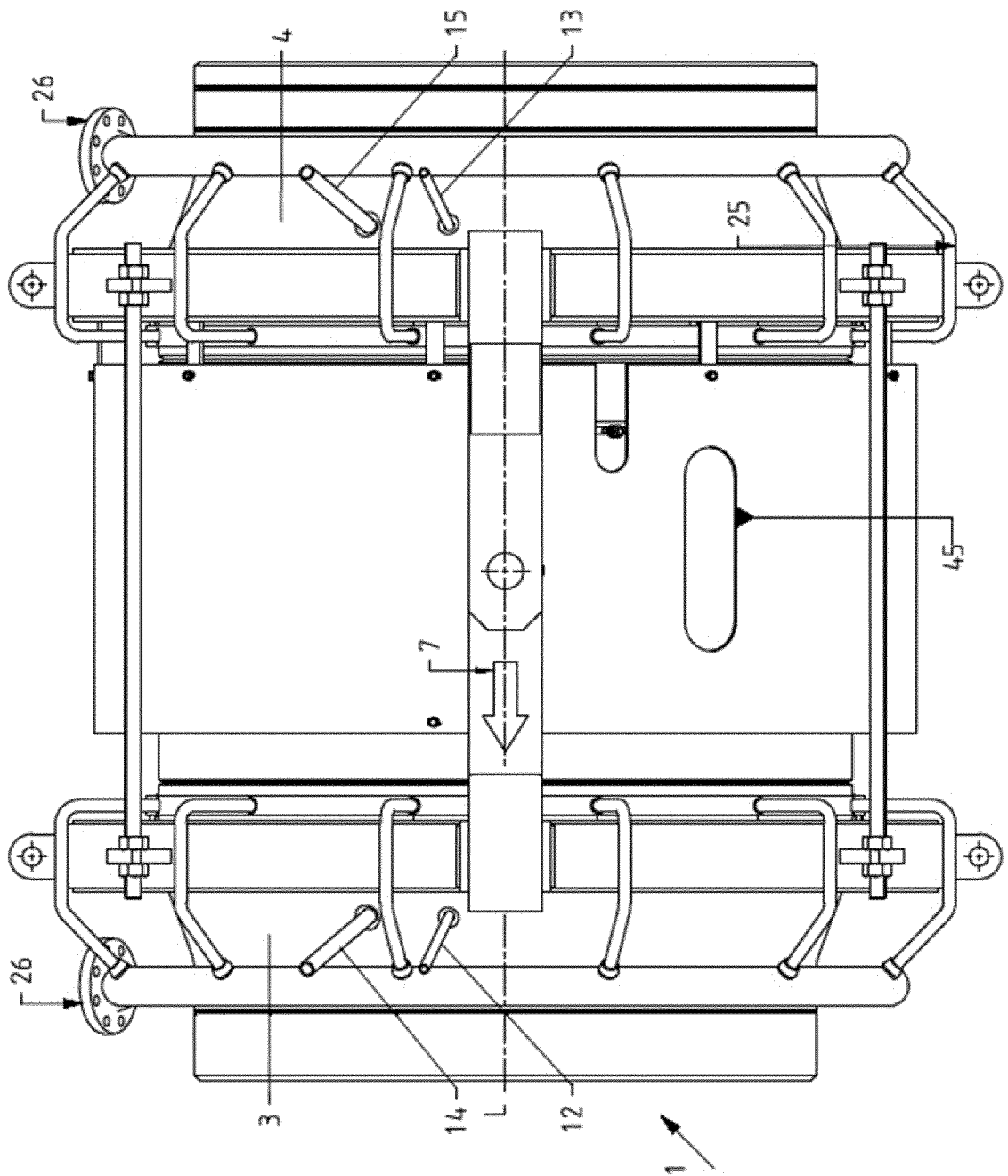
FIG. 2 shows a first side view of the expansion joint as per FIG. 1.
Figure 3:
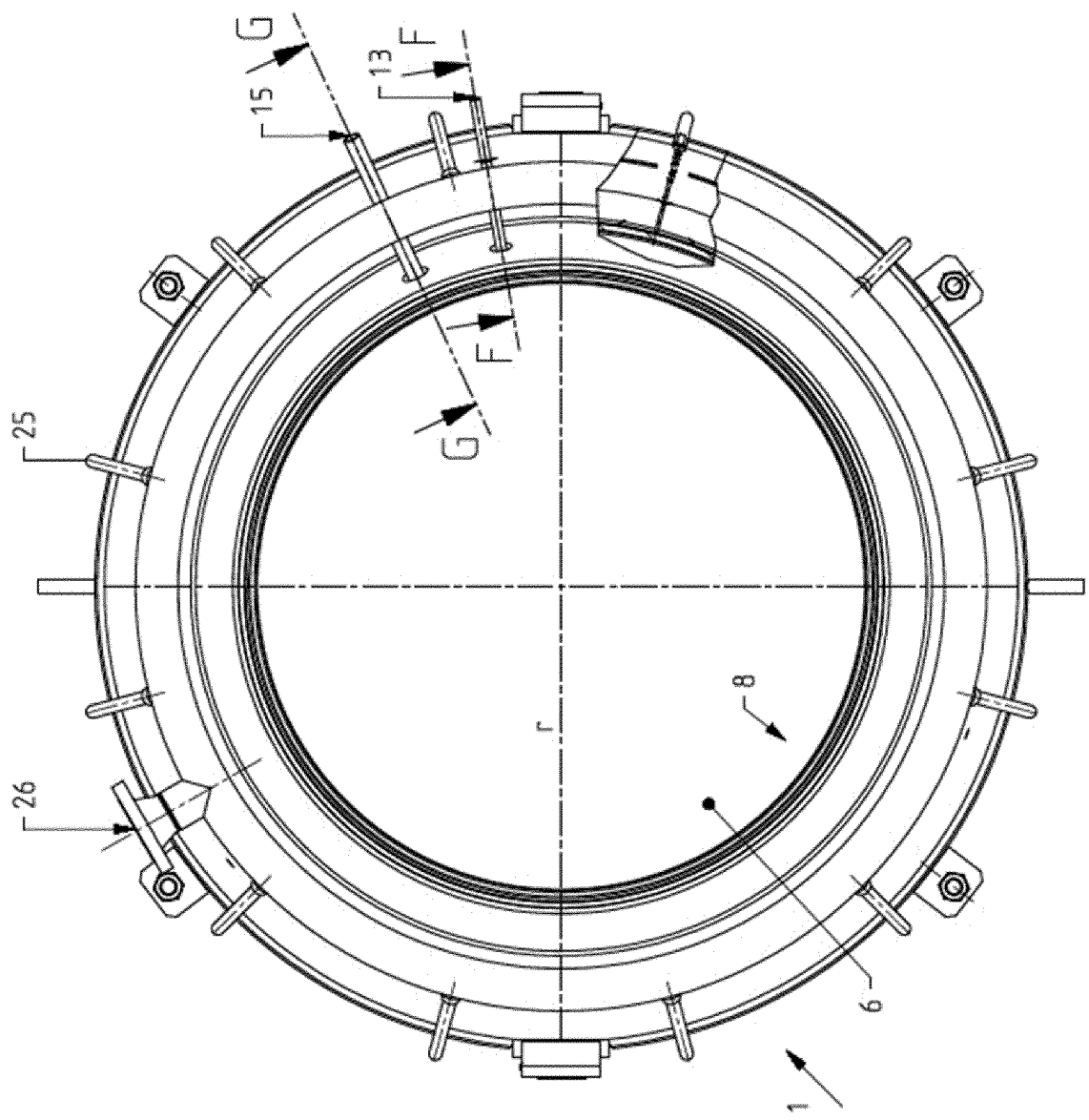
FIG. 3 shows a second side view of the expansion joint as per FIG. 1.
Figure 4:
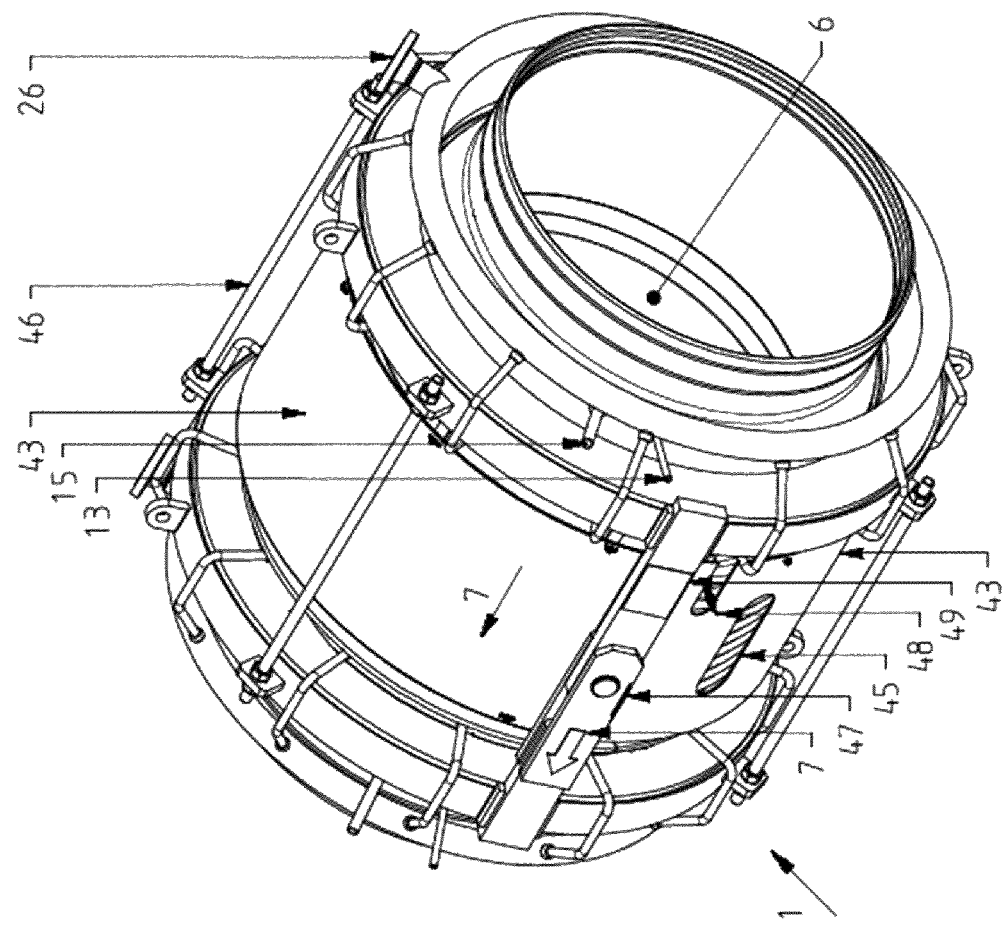
FIG. 4 shows a perspective view of the expansion joint as per FIG. 1.

FIGS. 1 to 10 show an embodiment of an expansion joint 1 according to the present invention. The cross-sectional view as per FIG. 1 is taken along B-B in FIG. 3. The expansion joint 1 is adapted for joining a first part of a pipe (not shown) to a second part of the pipe (not shown). In particular, the pipe and the expansion joint 1 can be parts of a plant for producing propylene from propane gas.

The expansion joint 1 comprises an expanded wall 2 having a first wall part 3, e.g. made of stainless steel, and a second wall part 4, e.g. made of stainless steel. The first wall part 3 can be connected to the first part of the pipe, and the second wall part 4 can be connected to the second part of the pipe. Alternatively, the first wall part 3 can be an integral part of the first part of the pipe, and the second wall part 4 can be an integral part of the second part of the pipe.

The first wall part 3 and the second wall 4 part are spaced apart from each other in an axial direction L of the expansion joint 1 by an axial gap. An expansion bellows 5 is welded onto the first wall part 3 with a weld seam a, and welded onto the second wall part 4 with a weld seam b, such that the axial gap between the first wall part 3 and the second wall part 4 is closed by the expansion bellows 5. The expansion bellows 5 is designed particularly in such a way that it enables to compensate relative movements of the parts of the pipe which are joint via the expansion joint 1.

In other words, the first wall part 3 and the second wall part 4 are connected flexibly by means of the expansion bellows 5, meaning that the first wall part 3 and the second wall part 4 are connected such that stresses caused by axial, angular or lateral movements between the first wall part 3 and the second wall part 4 can be compensated for, wherein said movements can occur due to high temperatures while hot propylene gas is led through a flow channel 6 within the expansion joint 1 during producing propylene from propane gas. An intended flow direction of propane gas through the flow channel 6 is indicated by arrow 7 in FIGS. 2 and 4. The flow channel 6 is limited in a radial direction r by an inner sleeve assembly 8.

The inner sleeve assembly 8 can comprise a first metal part 8.1, e.g. made of stainless steel, and a second metal part 8.2, e.g. made of stainless steel. The expanded wall 2 and the inner sleeve assembly 8 limit at least one sealed chamber 9, 10 between each other, and the at least one sealed chamber 9, 10 is adapted to be filled and pressurised by a first gas or a first sort of gas, respectively. In the shown example, the first sort of gas may be nitrogen.

Figure 7:
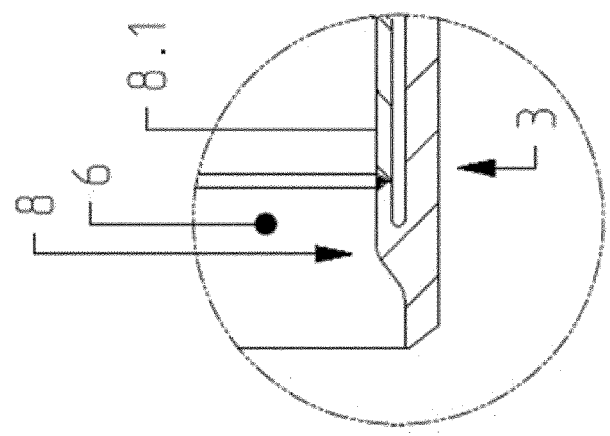
FIG. 7 shows an enlarged view of detail C of the expansion joint as per FIG. 1.

In the shown example, the first metal part 8.1 is connected to the first wall part 3 such that the first metal part 8.1 and the first wall part 3 limit a first sealed chamber 9 between each other, wherein the first sealed chamber 9 is filled by the first sort of gas. Preferably, the first sealed chamber 9 is adapted to be filled and pressurised by the first sort of gas. Particularly referring to FIG. 7, a part of the inner sleeve assembly 8 and the first wall part 3 are shown in an enlarged view. As can be seen from the example shown by FIG. 7, the inner sleeve assembly 8, in particular the first metal part 8.1 of the inner sleeve assembly 8, and the expanded wall 2, in particular the first wall part 3 of the expanded wall 2, can at least partly be formed integrally as a one piece element. In other words, especially the first metal part 8.1 of the inner sleeve assembly 8 can be connected to the first wall part 3 in a one-piece manner. Furthermore, FIG. 7 shows a weld preparation bevel to allow for sound welding over a full thickness of the joined parts (full penetration welds).

Figure 8:
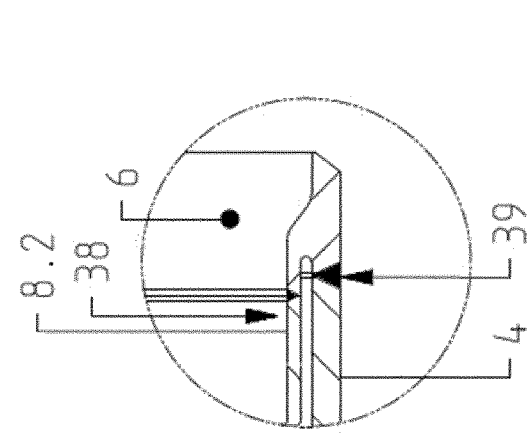
FIG. 8 shows an enlarged view of detail D of the expansion joint as per FIG. 1.

Similarly, the second metal part 8.2 is connected to the second wall part 4 such that the second metal part 8.2 and the second wall part 4 limit a second sealed chamber 10 between each other, wherein the second sealed chamber 10 is filled and by the first sort of gas. Preferably, the second sealed chamber 10 is adapted to be filled and pressurised by the first sort of gas. Particularly referring to FIG. 8, the second wall part 4 and the second metal part 8.2 can be two separated elements. Furthermore, FIG. 8 shows a weld preparation bevel to allow for sound welding over a full thickness of the joined parts (full penetration welds).

As shown in FIG. 1, the first sealed chamber 9 and the second sealed chamber 10 can partly be filled with insulating material 11. In the context of the first sealed chamber 9 and the second sealed chamber 10, the feature "sealed" especially can mean that said chambers 9 and 10 are built such that the first gas—by which the chambers 9 and 10 are pressurised—cannot leave the chambers 9 and 10. The first sealed chamber 9 and the second sealed chamber 10 can be designed substantially the same and can be arranged in mirror symmetry to each other as shown per FIG. 1.

The expansion joint 1 can further comprise first means 12 for sensing pressure and second means 13 for sensing pressure (FIGS. 2 to 5). Furthermore, the expansion joint one can comprise first gas supply means 14 and second gas supply means 15 (FIGS. 2 to 4 and 6).

Figure 5:
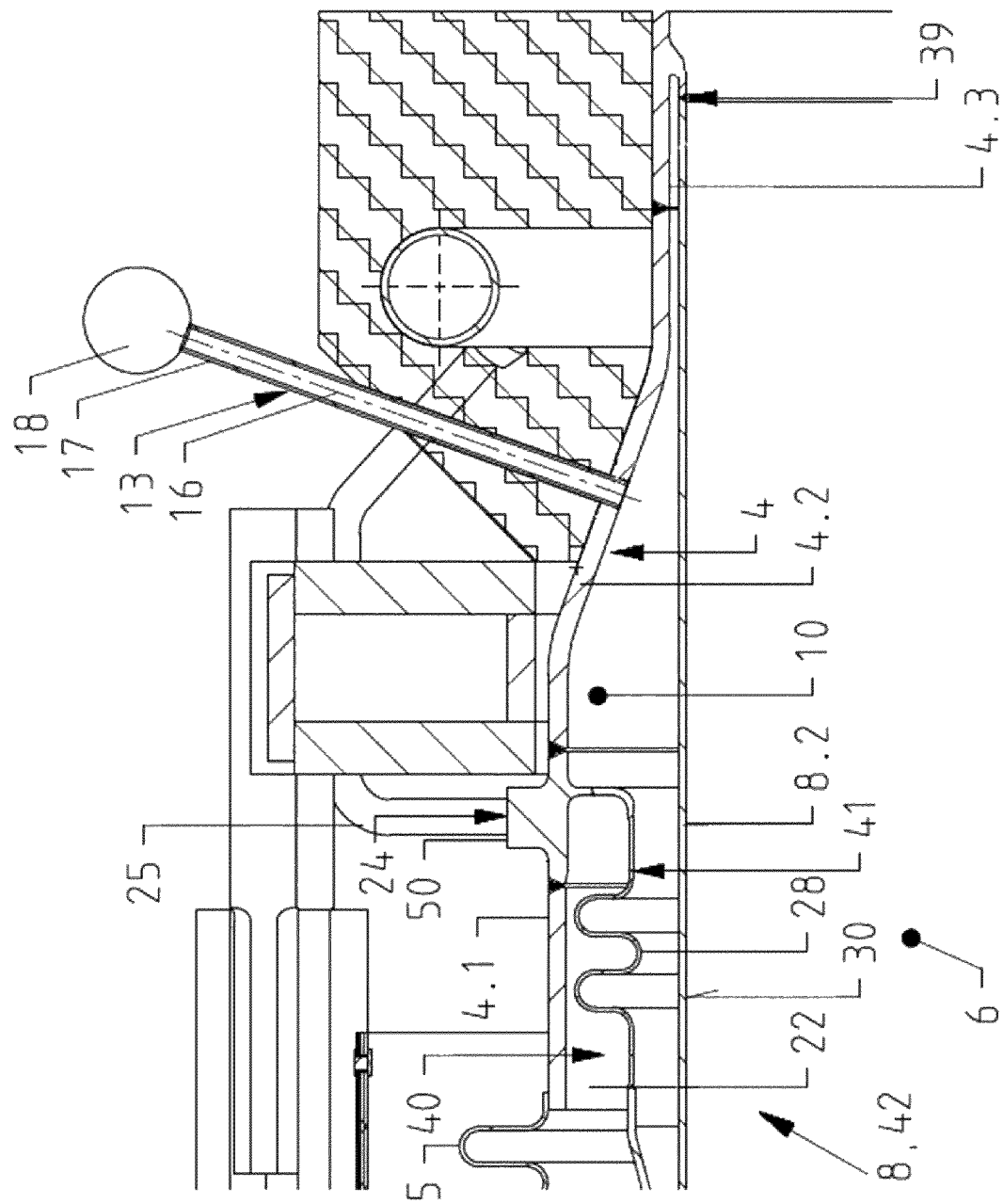
FIG. 5 shows a cross-sectional view of the expansion joint as per FIG. 1 taken along F-F in FIG. 3.
Figure 6:
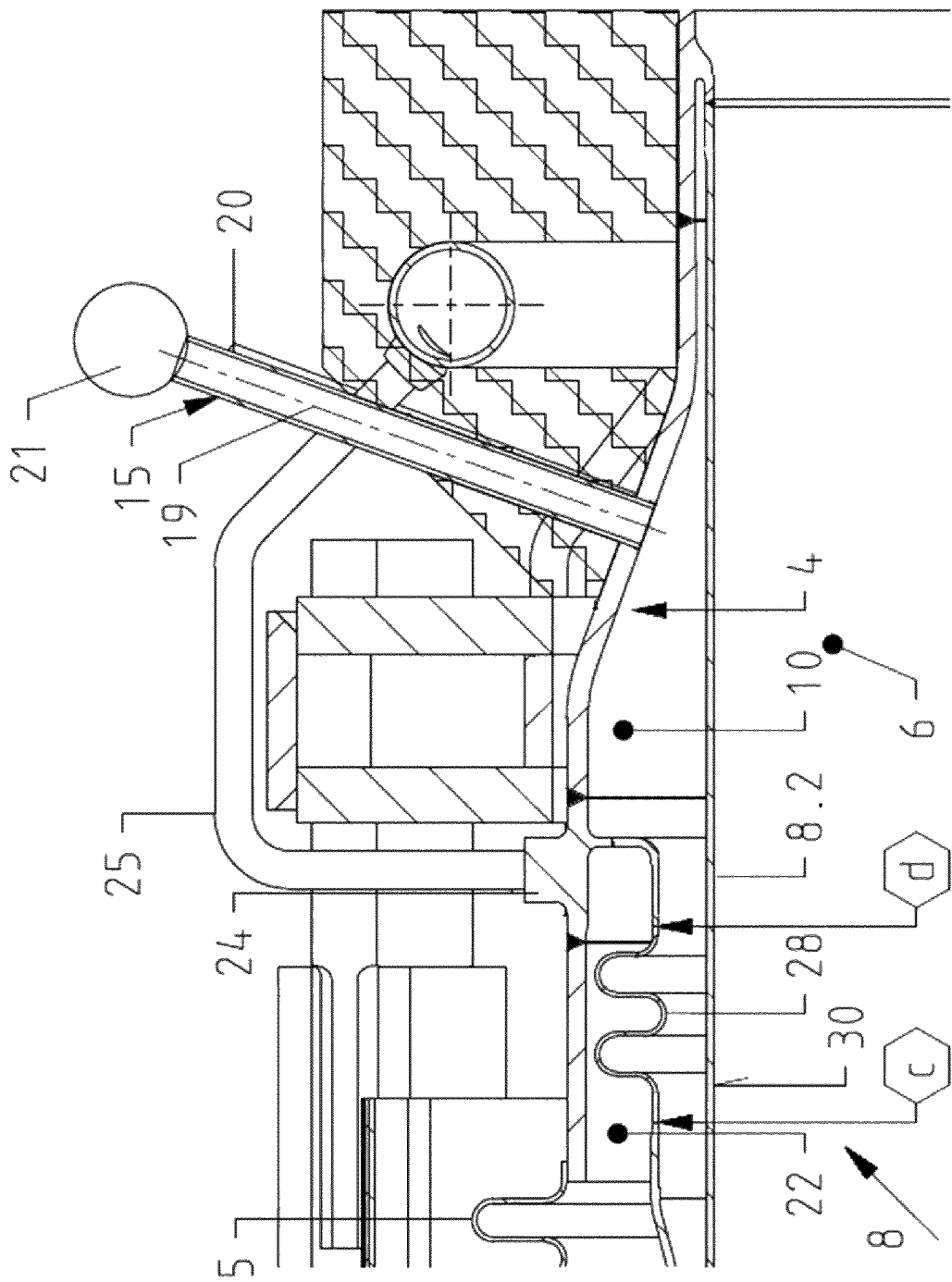
FIG. 6 shows a cross-sectional view of the expansion joint as per FIG. 1 taken along G-G in FIG. 3.

Particularly referring to FIGS. 5 and 6, the second chamber 10 is shown in an enlarged view, wherein the insulating material 11 is not shown for purposes of simplicity.

FIG. 5 shows the second means 13 for sensing pressure. According to the example shown by FIG. 5, the second means 13 for sensing pressure can comprise a connection channel 16, e.g. formed by a connection pipe 17. A first end of the connection channel 16 can be in a fluid connection with the second chamber 10. A second end of the connection channel 16 can be in a fluid connection with a pressure sensor 18 (shown in FIG. 5). The second means 13 for sensing pressure are adapted for measuring a second pressure within the second sealed chamber 10. The first means 12 for sensing pressure can be designed similarly and are adapted for measuring a first pressure within the first sealed chamber 9.

FIG. 6 shows the second gas supply means 15 which can comprise a supply channel 19, e.g. formed by a supply pipe 20. A first end of the supply channel 19 can be in a fluid connection with the second chamber 10. A second end of the supply channel 19 can be in a fluid connection with a reservoir 21 (only shown schematic in FIG. 6) for storing the first gas in a pressurised manner. The fluid connection between the supply channel 19 and the reservoir 21 can be controlled such that first gas stored within the reservoir 21 can leave the reservoir 21 and fill as well as pressurise the second chamber 10. In this way, the second gas supply means 15 are adapted for filling and pressurising the second sealed chamber 10 with the first gas. The first gas supply means 14 can be designed similarly and are adapted for pressurising the first sealed chamber 9 with the first gas.

A third chamber 22 is located between the first sealed chamber 9 and the second sealed chamber 10. The third chamber 22 can be limited by the first metal part 8.1 and the second metal part 8.2 of the inner sleeve assembly 8, the first wall part 3 and the second wall part 4 of the expanded wall 2 and the expansion bellows 5.

As shown by FIG. 1, the third chamber 22 can be separated from the first sealed chamber 9 by a first retaining ring assembly 23 on the one side (which is shown left in FIG. 1) and by a second retaining ring assembly 24 on the other side (which is shown right in FIG. 1), wherein both retaining ring assemblies 23 and 24 can comprise a monolithic part 50. FIGS. 5 and 6 show the second retaining ring assembly 24 in an enlarged view, wherein the second retaining ring assembly 24 is arranged between the second wall part 4 of the expanded wall 2. The first retaining ring assembly 23 is designed and arranged within the first wall part 3 of the expansion bellows 5 similarly.

In particular, the second wall part 4 can comprise a first section 4.1 with a gap which is filled by the second retaining ring assembly 24. The expansion bellows 5 can be welded onto one end (which is shown left in FIGS. 5 and 6) of the first section 4.1 by the second weld seam b. Furthermore, the second wall part 4 can comprise a second section 4.2 and a third section 4.3. The third section 4.3 can be connected to the part of the pipe which is to be joined by the expansion joint 1. The diameter of the first section 4.1 is larger than the diameter of the third section 4.3. The second section 4.2 is inclined with regards to the first section 4.1 and the third section 4.3. The second section 4.2 connects the first section 4.1 to the third section 4.3. The first wall part 3 can comprise a first section 3.1 (FIG. 10), a second and a third section similarly as can be seen from FIGS. 1 and 10.

The third chamber 22 can be filled and pressurised with a second gas, e.g. with propane gas, such that an over pressure within the third chamber 22 is higher than a process pressure of the second gas flowing across the flow channel 6 of the expansion joint 1. The third chamber 22 is in fluid connection with the flow channel 6. Therefore, second gas from within the third chamber 22 can leave the third chamber 22 and enter the flow channel 6. Due to the higher pressure within the third chamber 22 compared to the flow channel 6, second gas from within the flow channel 6 is hindered to enter the third chamber 22. In other words, the third chamber 22 is filled with and pressurised by second gas, such that this second gas builds a barrier flow for second gas within the flow channel 6. By this, the third chamber 22 acts as an hyperbaric pressure chamber compared to the flow channel 6.

A plurality of purge channels 25 can be in a fluid connection with the third chamber 22 on the one end and in a fluid connection with second gas supply connections 26 on the other ends. The purge channels 25 can be welded onto by fifth weld seams e and extend through the first retaining ring assembly 23 (FIG. 10) and the second retaining ring assembly 24. The second gas supply connections 26 can be connected to a reservoir (not shown) for storing second gas in a pressurised manner. The fluid connection between the purge channels 25 and said reservoir can be controlled such that second gas stored within the reservoir can leave the reservoir and fill as well as pressurise the third chamber 22. In this way, the third chamber 22 can be pressurized with second gas.

The first metal part 8.1 can comprise a first additional bellows 27 (FIG. 10) and the second metal part 8.2 can comprise a second additional bellows 28 (FIGS. 5 and 6). The second additional bellows 28 is welded onto the second metal part 8.2 by a third weld seam c and onto the second retaining ring assembly 24 by a fourth weld seam d (FIG. 6). Similarly, the first additional bellows 27 is welded onto the first metal part 8.1 by a weld seam and onto the first retaining ring assembly 23 by a weld seam. The additional bellows 27 and 28 help to compensate for stresses that the first metal part 8.1 and the second metal part 8.2 (which can be relatively thin compared to the first wall part 3 and second wall part 4) are subjected to, in particular in areas of a first interior wall surface 29 of the inner sleeve 8 and a second interior wall surface 30 of the inner sleeve 8.

Figure 9:
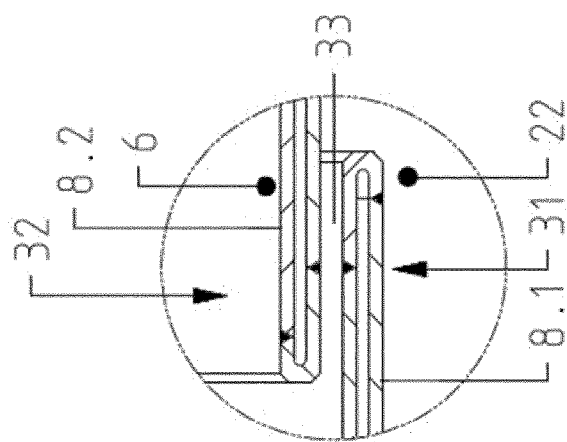
FIG. 9 shows an enlarged view of detail E of the expansion joint as per FIG. 1.

As can best be seen in FIG. 9, the first metal part 8.1 can be bent 180° in a first bending area 31 and the second metal part 8.2 can be bent 180° in a second bending area 32, wherein the first bending area 31 of the first metal part 8.1 overlaps the second bending area 32 of the second metal part 8.2 such that pressurised gas from within the third chamber 22 can flow out of the third chamber 22 into the flow channel 6. In particular, there can be a radial gap between the first bending area 31 of the first wall part 3 and the second bending area 32 of the second wall part 4 such that a connection channel 33 for the gas is built that allows gas from within the third chamber 22 to exit the third chamber 22 and to enter the flow channel 6 via said connection channel 33.

Figure 10:
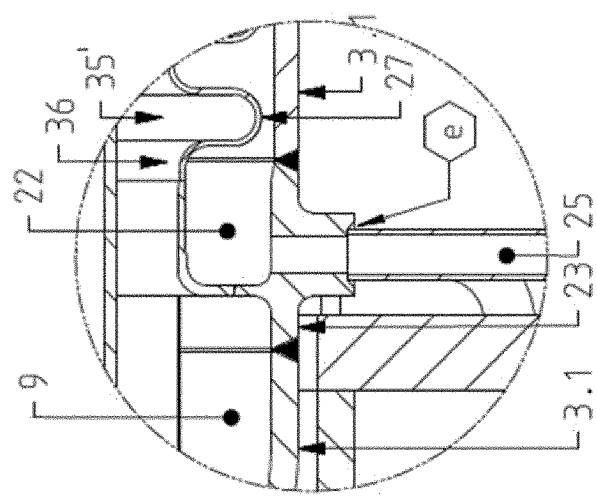
FIG. 10 shows an enlarged view of detail H of the expansion joint as per FIG. 1.

As can be seen from FIG. 1 a first end 34 of the first metal part 8.1 can be welded onto the first wall part 3 at a first connection position 35. A second end 35' of the first metal part 8.1, in particular its first additional bellows 27, can be connected to the first wall part 3, in particular to its first retaining ring assembly 23, at a second connection position 36 (FIG. 10). A first portion 37 of the first metal part 8.1 between the first connection position 35 and the first bending area 31 provides the first interior wall surface 29 of the flow channel 6 (FIGS. 1 and 9).

Similarly, as can be seen e.g. from FIGS. 5, 6 and 8, a first end 38 of the second metal part 8.2 can be connected to the second wall part 4 at a third connection position 39. A second end 40 of the second metal part 8.2, in particular its second additional bellows 28, can be connected to the second wall part 4, in particular to its second retaining ring assembly 24, at a fourth connection position 41. A first portion 42 of the second metal part 8.2 starting from the third connection position 39 and extending up to and including the second bending area 32 provides the second interior wall surface 30 of the flow channel 6.

Particularly referring to FIG. 1, the expansion joint 1 can further comprise a removable cover 43 for protection during transportation and against environmental influences. Also, an outer insulation 44 can be provided which surrounds the expanded wall 2. Particularly referring to FIG. 2, the expansion joint 1 can further comprise an inspection hole 45. Particularly referring to FIG. 4, the expansion joint 1 can further comprise tie rods 46 as a transportation safety guard, wherein the tie rods 46 have to be removed before start up. Also, axial movement indicators 47 can be provided as well as an interply monitoring connection 48 and a nameplate 49. The bellows 5 can be composed of several thin metal layers, so called 'plies'. The interply monitoring connection 48 enables an interply monitoring in order to detect eventual leaks in one of the plies, wherein such leaks may not be detectable from the outside. Additional weld seams are indicated with hexagons within the drawings.

REFERENCE SIGNS a first weld seam
b second weld seam c third weld seam
d fourth weld seam
e fifth weld seam
L axial direction
r radial direction
1 expansion joint
2 expanded wall
3 first wall part
3.1 first section of the first wall part
4 second wall part
4.1 first section of the second wall part
4.2 second section of the second wall part
4.3 third section of the second wall part
5 expansion bellows
6 flow channel
7 arrow flow direction
8 inner sleeve assembly
8.1 first metal part
8.2 second metal part
9 first sealed chamber
10 second sealed chamber
11 insulation material
12 first means for sensing pressure
13 second means for sensing pressure
14 first gas supply means
15 second gas supply means
16 connection channel
17 connection pipe
18 pressure sensor
19 supply channel
20 supply pipe
21 reservoir for storing the first gas
22 third chamber
23 first retaining ring assembly
24 second retaining ring assembly
25 purge channel
26 propane gas supply connections
27 first additional bellows
28 second additional bellows
29 first interior wall surface
30 second interior wall surface
31 first bending area
32 second bending area
33 connection channel
34 first end of the first metal part
35 first connection position
35' second end of the first metal part
36 second connection position
37 first portion of the first metal part
38 first end of the second metal part
39 third connection position
40 second end of the second metal part
41 fourth connection position
42 first portion of the second metal part
43 removable cover
44 outer insulation
45 inspection hole
46 tie rod
47 axial movement indicator
48 interply monitoring connection
49 nameplate
50 monolithic part

The invention claimed is:

1. An expansion joint for joining two adjacent parts of a pipe, the expansion joint comprising:
an expansion bellows,
an expanded wall and
an inner sleeve assembly,
wherein
the expanded wall comprises a first wall part and a second wall part, wherein the first wall part and the second wall part are spaced apart from each other axially by an axial gap,
the expansion bellows is connected to the first wall part and to the second wall part such that the axial gap between the first wall part and the second wall part is closed and such that the first wall part and the second wall part are connected flexibly,
the expanded wall and the inner sleeve assembly limit at least one sealed chamber between each other, and
the at least one sealed chamber is filled by a first gas, and wherein
the inner sleeve assembly comprises a first metal part and a second metal part, wherein
the first metal part is connected to the first wall part such that the first metal part and the first wall part limit a first sealed chamber between each other,
the second metal part is connected to the second wall part such that the second metal part and the second wall part limit a second sealed chamber between each other, and
the first sealed chamber and the second sealed chamber are adapted to be filled and pressurised by the first gas, and wherein
the inner sleeve assembly, the expanded wall and the expansion bellows limit a third chamber between each other,
the third chamber is in fluid connection with a flow channel, wherein the flow channel is limited by the inner sleeve assembly, and
the third chamber is adapted to be filled and pressurized with a second gas, such that an over pressure within the third chamber is higher than a process pressure of the second gas within the flow channel within the expansion joint.

2. The expansion joint according to claim 1, wherein the at least one sealed chamber is filled with insulating material.

3. The expansion joint according to claim 1, wherein:
the first metal part comprises a first additional bellows and
the second metal part comprises a second additional bellows.

4. The expansion joint according to claim 1, wherein:
the first wall part comprises a first retaining ring assembly,
the second wall part comprises a second retaining ring assembly,
the first retaining ring assembly separates the first sealed chamber from the third chamber, and
the second retaining ring assembly separates the second sealed chamber from the third chamber.

5. The expansion joint according to claim 1, wherein:
the first metal part is bent 180° in a first bending area,
the second metal part is bent 180° in a second bending area, and
the first bending area of the first metal part overlaps the second bending area of the second metal part such that pressurised second gas from within the third chamber can flow out of the third chamber into the flow channel.

6. The expansion joint according to claim 5, wherein:
a first end of the first metal part is connected to the first wall part at a first connection position,
a second end of the first metal part is connected to the first wall part at a second connection position,
a first portion of the first metal part between the first connection position and the first bending area provides a first interior wall surface of the flow channel, a first end of the second metal part is connected to the second wall part at a third connection position, a second end of the second metal part is connected to the second wall part at a fourth connection position, and a first portion of the second metal part between the third connection position and the second bending area provides a second interior wall surface of the flow channel.

7. The expansion joint according to claim 1, the expansion joint further comprising first means for sensing pressure and second means for sensing pressure, wherein the first means for sensing pressure are adapted for measuring a first pressure within the first sealed chamber, and wherein the second means for sensing pressure are adapted for measuring a second pressure within the second sealed chamber.

8. The expansion joint according to claim 1, wherein the expansion joint further comprises first gas supply means and second gas supply means, wherein the first gas supply means are adapted for filling the first sealed chamber with the first gas, and wherein the second gas supply means are adapted for filling the second sealed chamber with the first gas.

9. The expansion joint according to claim 8, the expansion joint further comprising third gas supply means, wherein the third gas supply means are adapted for filling and pressurising the third chamber up to the over pressure with the second gas.

10. The expansion joint according to claim 1, wherein the first gas is nitrogen.

11. The expansion joint according to claim 1, wherein the second gas is propane gas.

12. The expansion joint according to claim 1, wherein the inner sleeve assembly, and the expanded wall can at least partly be formed integrally as a one piece element.

13. Plant for producing propylene from propane gas, the plant comprising a first part of a pipe, a second part of the pipe and an expansion joint according to claim 1, wherein the first part of the pipe is joined to the second part of the pipe by means of the expansion joint.

\* \* \* \* \*